United States Patent
Cruitt et al.

(10) Patent No.: US 7,607,431 B1
(45) Date of Patent: Oct. 27, 2009

(54) MEDICAL REMINDER DEVICE SUITED FOR USE WITH NEBULIZERS

(76) Inventors: Stanley L. Cruitt, 525 Roslyn Rd., Winston-Salem, NC (US) 27104; Sidney Chan, 3062 SW. Marine Drive, Vancouver, BC (CA) V6N 3Y3; Jaroslav V. Tichy, 7128 Brewster Drive West, Delta, BC (CA) V4E 1V2

( * ) Notice: Subject to any disclaimer, the term of this patent is extended or adjusted under 35 U.S.C. 154(b) by 623 days.

(21) Appl. No.: 11/351,432

(22) Filed: Feb. 10, 2006

Related U.S. Application Data

(60) Provisional application No. 60/652,237, filed on Feb. 11, 2005.

(51) Int. Cl.
*A61M 11/00* (2006.01)
(52) U.S. Cl. .............. 128/200.14; 128/200.21; 128/203.27
(58) Field of Classification Search ............ 368/10; 128/200.14, 203.14
See application file for complete search history.

(56) References Cited

U.S. PATENT DOCUMENTS

| | | | |
|---|---|---|---|
| 4,490,711 A | 12/1984 | Johnston | |
| 6,018,289 A | 1/2000 | Sekura | |
| 6,050,940 A | 4/2000 | Braun et al. | |
| 6,075,755 A * | 6/2000 | Zarchan | 368/10 |
| 6,190,326 B1 | 2/2001 | McKinnon et al. | |
| 6,198,383 B1 | 3/2001 | Sekura et al. | |
| 6,351,207 B1 | 2/2002 | Mik et al. | |
| 6,390,091 B1 | 5/2002 | Banner et al. | |
| 6,421,650 B1 * | 7/2002 | Goetz et al. | 705/3 |
| 6,723,046 B2 | 4/2004 | Lichtenstein et al. | |
| 2004/0065321 A1 * | 4/2004 | Stenzler | 128/200.14 |

OTHER PUBLICATIONS

Ormon Instruction Manuel, CompAir XL, Compressor Nebulizer System Model NE-C18, CopyrightFeb. 2002.

* cited by examiner

*Primary Examiner*—Steven O Douglas
(74) *Attorney, Agent, or Firm*—Robert W. Pitts

(57) ABSTRACT

A reminder device 2 and a system using that device can be employed both to alert a user to scheduled times for administration of standard medical procedures and to compile data representative of the actual administration of the medical procedure. The reminder device 2 includes an LCD 8 for notifying a user of important messages. The reminder device can be connected to a communications network so that data can be downloaded to the reminder device and uploaded to a medical professional for analysis. The reminder device can also be attached to a medical apparatus, such as a nebulizer, and the intervals during which that medical apparatus are in actual use can be communicated to and stored in the reminder device memory for subsequent uploading to a medical professional.

24 Claims, 9 Drawing Sheets

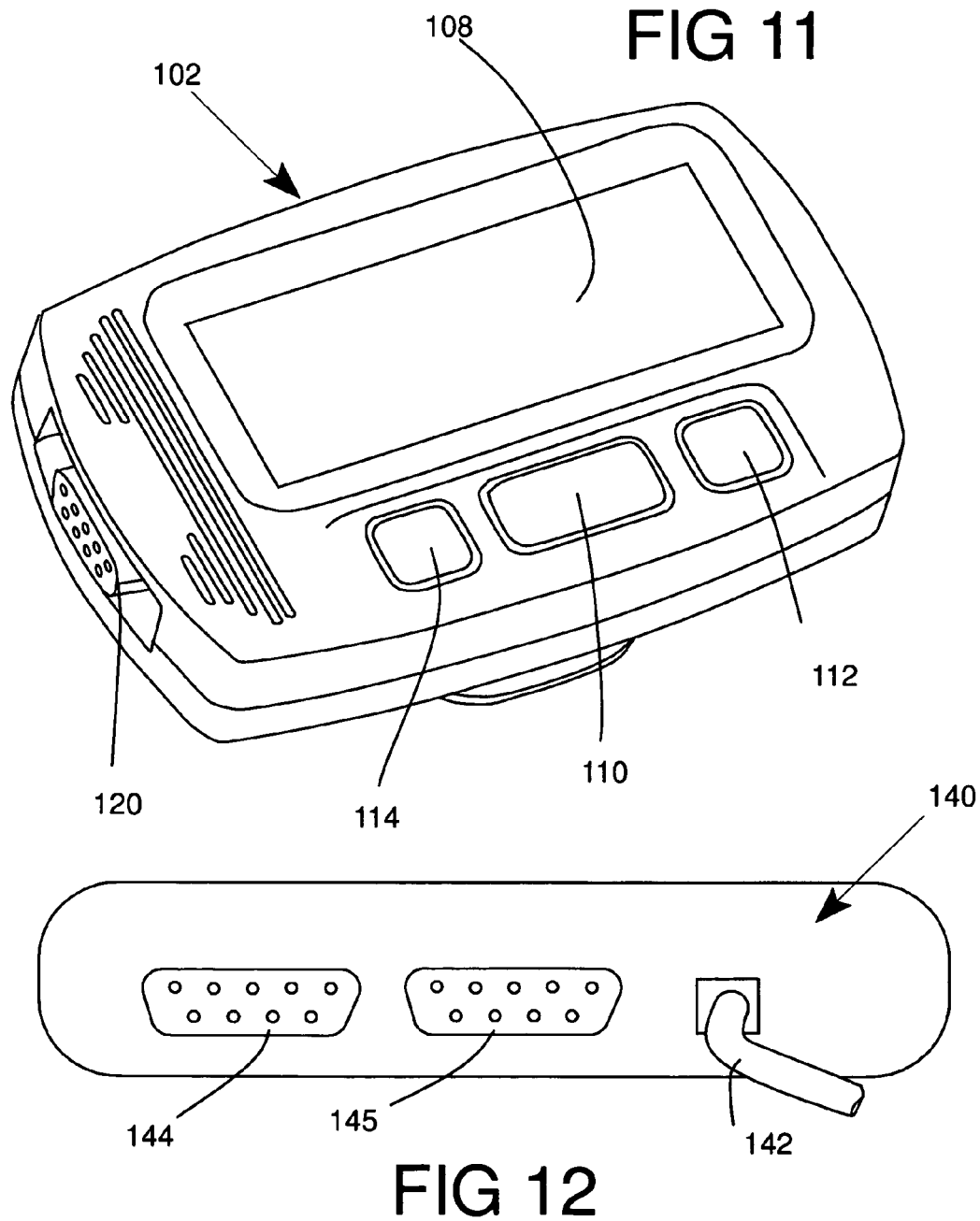

MEDICAL REMINDER DEVICE SUITED FOR USE WITH NEBULIZERS

CROSS REFERENCE TO PRIOR CO-PENDING APPLICATION

This application claims the benefit of prior U.S. Provisional Patent Application 60/652,237 filed Feb. 11, 2005 entitled Medical Reminder Device Suited for Use with Nebulizers.

BACKGROUND OF THE INVENTION

1. Field of the Invention

This invention is related to devices and systems that can be used to remind a person of a scheduled medical procedure. This invention is also related to the storage and retrieval of information relevant to the actual performance of a medical procedure so that this data can be reviewed by a medical professional. This invention is also related to the use of a medical treatment device, such as a nebulizer, and to a device for alerting a user to use the nebulizer as well as storing information indicative of the time and extent of use of the nebulizer.

2. Description of the Prior Art

Increasingly sophisticated medical procedures and medical care can now be performed in the home, either by a patient or a care giver, who typically is not medically trained. In order to insure that medical care is being properly administered or has been properly administered, there is a need for providing information or data, representative of actual administration of medical procedures, including administration of prescribed medications according to a proper schedule, to a medical professional. Historical data relevant to these medical procedures can be quite useful by a medical professional to determine if the procedure has been properly administered and if a medical problem may be due to inadequate performance of prescribed medical care. For instance, a record indicative of actual use of prescribed medications can be helpful to doctors, who might determine that the patient's problem is exacerbated by his failure to take his or her medications on a proper schedule.

One approach to collect data relevant to medical procedures and the medical condition of a patient is to employ an interface device to connect one or more medical instruments to a central database. Data accumulated by these medical instruments can be transmitted through the interface device over a standard network, such as a telecommunications network or over the Internet to a medical database, which can store data from multiple instruments and from multiple interface devices, which can typically serve multiple patients, users or care givers. An example of one such system is shown in U.S. Pat. No. 6,723,046. This system appears to contemplate regular transmission of data stored by medical instruments to the central database, typically by intervention of the user or patient.

Another approach is to use a prescription compliance device to record data relevant to performance of a prescribed medical procedure. U.S. Pat. No. 6,198,383 is one example of such an apparatus. The device shown therein is one that is normally programmed by the user. However, programming appears to be limited to pre-selected medication regimens, in order to simplify programming. Therefore, this device lacks flexibility when used to by a medical professional to remotely monitor medical care performed by a patient of other nonprofessional care giver. The device described therein does provide a wireless remote capability, but that capability appears to be primarily intended for use in an institutional environment.

Some prior art digital instruments read and record diagnostic data into personal computers. The patient or on-site caregiver must normally transmit that data, and these approaches normally do not provide any reminder to the patient or on-site caregiver to transmit that data to a medical professional at a remote location. There can then be a significant delay before the medical professional receives the data, and any treatment alteration will therefore be delayed. The instant device provides a reminder to the patient and on-site caregiver and can insure that data will be delivered no later than the next day.

The instant invention can be used in a system in which actual medical care can be administered by a patient or nonprofessional care giver, but one in which a medical professional can both program the device and remotely monitor stored information. The device, according to this invention can also be portable so that it can be physically transported to a medical professional for review of compliance data stored in the device memory. Furthermore, this device is intended to communicate directly with other medical devices, such as a nebulizer, so that the reminder device can not only alert the user of schedule times for using the nebulizer, but can also store data relevant to use of the apparatus, such as a nebulizer. Use of this portable device requires only minor modifications to the other medical apparatus, and the device can be used to alert the user to other medical procedures. Indeed, the patient's entire requirements for home medical care can be scheduled by use of this reminder device.

SUMMARY OF THE INVENTION

According to one aspect of this invention, a programmable reminder device is used in reminding a user of a scheduled medical procedure and for storing data representative of actual administration of the scheduled medical procedure. This device includes a microprocessor, with read only memory including instructions for operation of the reminder device, and read/write memory for storing times for administration of scheduled medical procedure, information identifying the medical procedure, instructions for the patient, data that may be obtained from medical instruments and data representative of actual administration of the medical procedure. The reminder device also includes a visible display in communication with the microprocessor for displaying information identifying the medical procedure. An alarm for prompting a user to administer the scheduled medical procedure and a switch for acknowledging the alarm are also included. An input port on the reminder device can be connected to an apparatus used in administering the medical procedure and to medical diagnostic instruments. Data representative of actual administration of the scheduled medical procedure can be stored in the device memory.

A system for use in collecting data representative of administration of medical procedures by a user and for transmitting such data to a medical professional for subsequent review of the course of administration of the medical procedures, includes the programmable reminder device. Data stored in accessible memory includes times for administration of scheduled medical procedures, information identifying the medical procedures, and data representative of administration of the medical procedures. The alarm on the programmable reminder device for notifies a user of scheduled times for administration of medical procedures stored in the read/write memory. The acknowledgment input on the programmable reminder device is actuated by a user to denote receipt of the alarm, and the time of each acknowledgment input is stored in the accessible memory. A communications interface device can be connected to the programmable reminder device and to an external communications network for downloading times for administration of scheduled medical procedures and information identifying the medical procedures to the programmable reminder device, and for uploading data stored in the read/write memory representative of alarm times and acknowledgment times for corresponding medical procedures in response to a downloaded request submitted through the external communications network.

According to another aspect of this invention the times and data associated with each scheduled medical procedure for which the user has not responded are stored in built in memory. The reminder device is programmed to include an alarm state into which the reminder device enters when each alarm is triggered, wherein the number of pending alarms are first displayed. Upon actuation of the user switches in response to an alarm, the reminder device displays messages associated with alarms with the last alarm having a first priority.

One use of this reminder device is part of a system for storing data representative of administration of a scheduled medical procedure in which an electrically powered medical apparatus is used to perform the medical procedure. The reminder device can be connected to the electrically powered medical apparatus by a cable. The cable is connected to the electrically powered medical apparatus so that a signal is transmitted to the electronic device when the on/off switch on the separate device is activated. The times of actuation of the on/off switch are stored in the accessible memory so that that interval during which the scheduled medical procedure is performed can be retrieved from memory. An acknowledgment switch on the reminder device is actuated at the time the scheduled medical procedure is initiated so that the stored interval can be associated with the correct medical procedure when the stored data is analyzed. In one embodiment of this invention the separate apparatus comprises a nebulizer and a double pole, single throw switch on the nebulizer is employed to separate the compressor power source form the data line extending to the reminder device.

BRIEF DESCRIPTION OF THE DRAWINGS

FIG. 11 is a view of an alternate embodiment of a reminder device.

FIG. 12 shows a communications unit that can be used with the reminder device shown in FIG. 11.

DETAILED DESCRIPTION OF THE PREFERRED EMBODIMENTS

Figure 1:
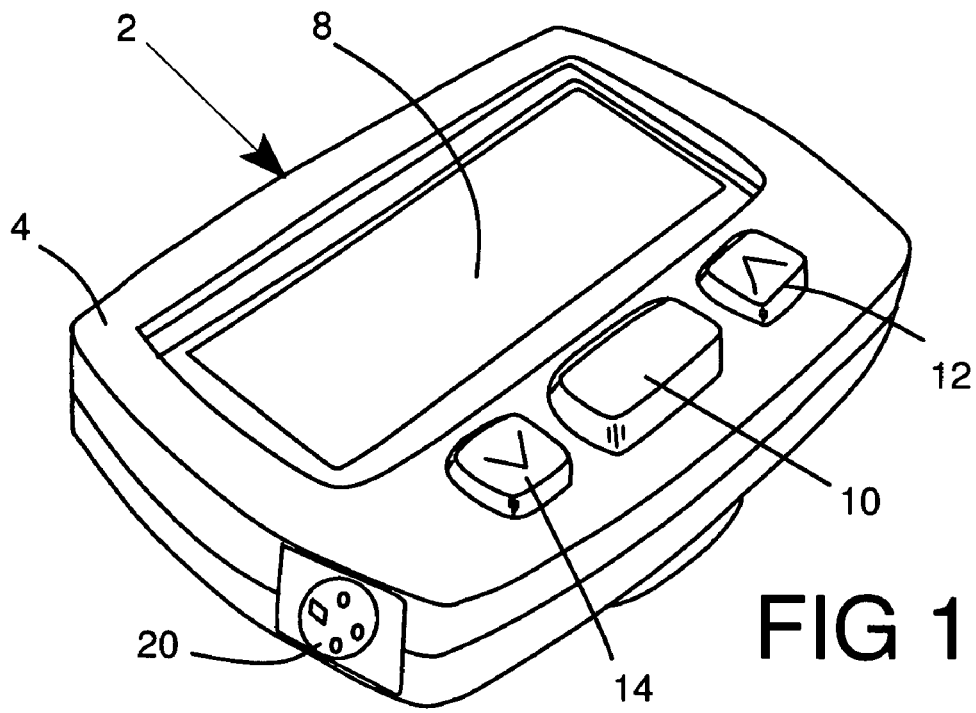
FIG. 1 is a view of a portable reminder device according to this invention in which an LCD for communicating with the user is shown.
Figure 2:
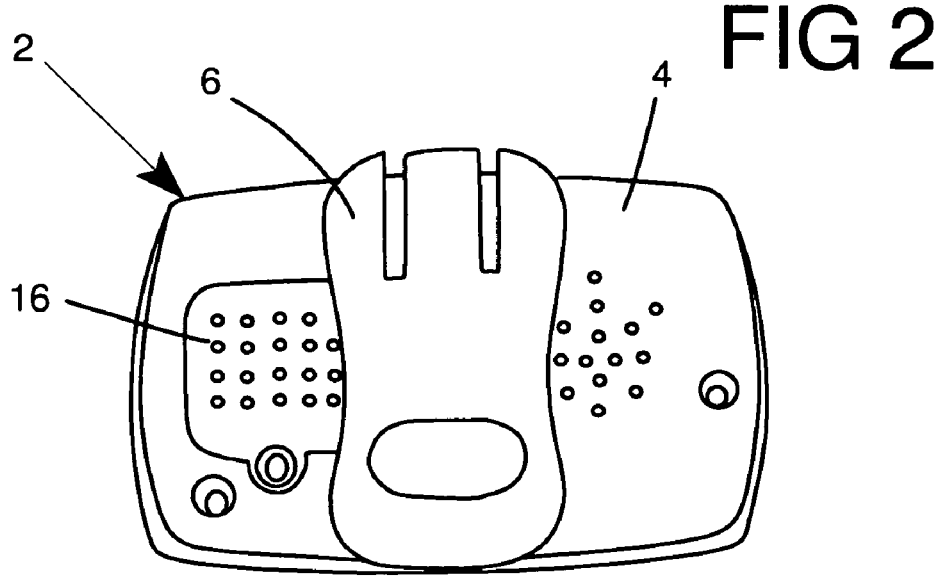
FIG. 2 is a view of the rear of the reminder device shown in FIG. 1.

FIGS. 1 and 2 show a reminder device 2 that can also store a compliance file including data representative of performance of a medical procedure. This reminder device 2 also serves as an interactive communications device that allows a remote medical professional to access this compliance file as well as to program or reprogram the device. In its preferred embodiment, reminder device 2 is battery powered and is portable. The dimensions of this device are approximately three and seven/sixteenth (3 7/16) inches by two and three/eights (2 3/8) inches, and the device has a height of approximately eleven/sixteenth (11/16) inch.

Reminder device 2 includes an LCD screen 8 on the front of a two piece molded housing 4. Actuators for three switches 10, 12 and 14 are accessible on the front of the device housing 4. A central actuator for an acknowledgment switch 10 is the primary user interface with the reminder device. This acknowledgment switch actuator 10 is larger than the other two switches because it serves as the primary user interface. The switch actuator 12 on the right comprises an Up switch for scrolling upward on the LCD 8, and the left switch actuator 14 functions as a Down actuator for the text displayed on LCD screen. In the preferred embodiment, each of these switches is accessible on the front of the reminder device 2 comprises a momentary push button switch. A two position slide switch, which is not visible in FIGS. 1 and 2 can be mounted along one edge of the device housing 4. A user, who can be a patient or care giver without significant medical training or computer skills, is able to operate the reminder device and the display on the LCD by using these switches. The three push button switches 10, 12 and 14 are the only switches that will be used during typical use of the device. The function of the two position slide switch is employed to temporarily deactivate the reminder device 2 in a manner that will be subsequently discussed in more detail.

The reminder device 2 can be attached to other devices by use of standard cables and connector configurations. FIG. 1 shows an electrical connector 20 on one edge of the housing 4. An external device cable 22 can be employed to connect the reminder device 2 to an external medical apparatus or instrument in the manner shown in FIGS. 9 and 10. A second standard connector, not shown in FIGS. 1 and 2 can be located along the opposite edge of the housing 4 to connect the reminder device 2 to a modem 40 or other communications interface also shown in FIGS. 9 and 10. The operational reminder functions of the device 2 are not dependent upon these external connections, but these subsidiary devices can be employed for upload and download communications, for programming, and for receiving data from the external device so that this data can be stored in the device memory. The device 2 will function to remind the user of a scheduled medical procedure in either its connected state or when disconnected from other external devices. Reminder device 2 is battery powered and can be portable. FIG. 2 shows the battery compartment 16 as well as a clip 6 located on the rear of the device. A user can clip the device to his or her belt or other apparel so that he or she will have the device when away from the location in which the external devices are normally resident. In this way the reminder device 2 retains all the essential functionality of basic reminder devices that have been previously employed to alert the user when to take medication or to perform some other activity.

Figure 3:
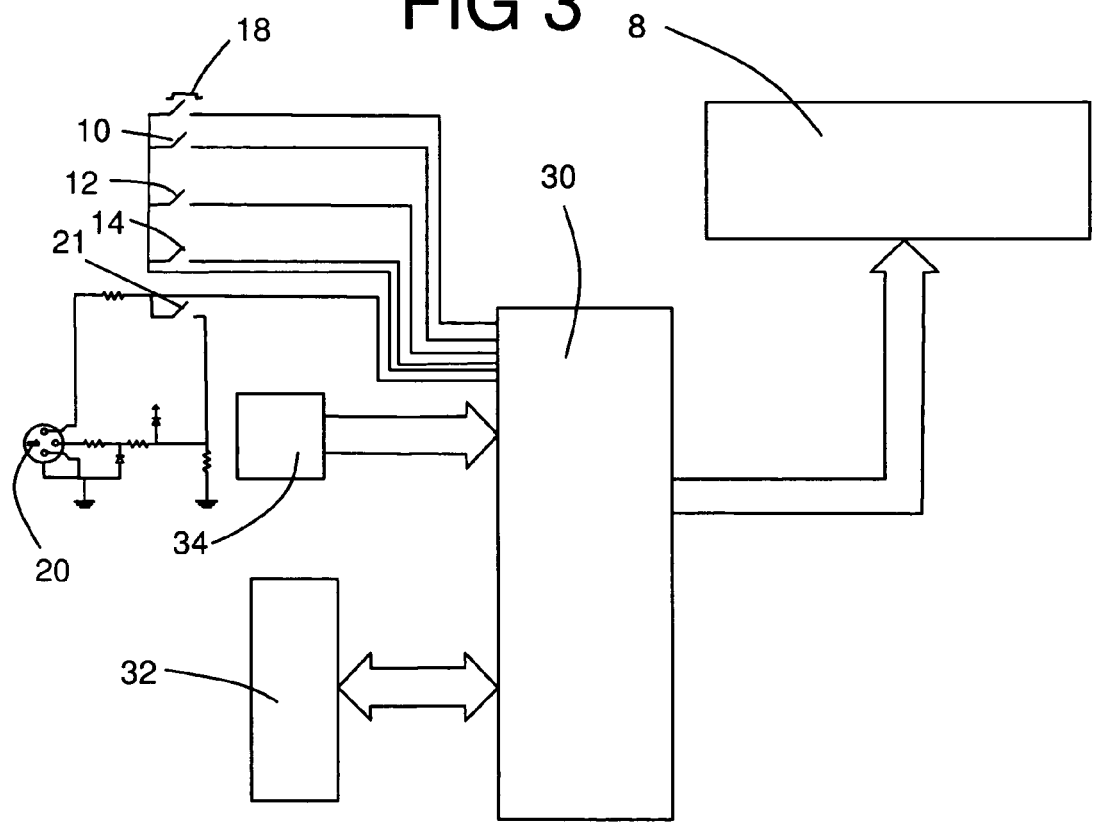
FIG. 3 is a view of an electrical schematic of the reminder device shown in FIGS. 1 and 2.

The schematic shown in FIG. 3 shows the basic components of the reminder device 2 and the manner in which switch activation can be used not only to change the device states, but also to store data representative of the performance of medical procedures. The reminder device includes a microprocessor 30, programmable memory 34, in this case standard EPROM, and read /write or random access memory 32, which interface with the microprocessor 30 according to the standard specifications of the microprocessor chosen for use in this reminder device 2. In the preferred embodiment, the microprocessor 30 comprises a CMOS 4-bit microcontroller with built-in 1024-dot matrix LCD drivers operating at 0.9 V (min). A liquid crystal device or LCD 8 is also employed to display alarms or messages that are stored in memory, and the choice of microprocessor 30 is largely dictated by its capabilities of outputting to an LCD having sufficient display. The Acknowledgment switch 10, the Up switch 12 and the down switch 14 are connected to input ports on the microprocessor 30 as shown. FIG. 3 also shows the slide switch 18, which is also connected to an input on the microprocessor 30. An input line on the external connector 20 is also connected to an input port on the microprocessor. This connector 20 will serve to connect a switch employed on an external device to an input port on the microprocessor 30. FIG. 3 also shows an auxiliary switch 21, which although not employed in the preferred embodiment of this invention, can be employed as an input switch in other configurations. The switch 21 can function as a pill box switch when this device is employed as incorporated into a pill box. It should be understood that switch 21 is not limited to use on a pill box, but can provide an input when the reminder device is incorporated as an integral part of another medical device. However, in the preferred embodiment of this invention, the reminder device 2 retains its separate character, and is only connected to another medical apparatus, such as a nebulizer, so that only minimal changes need be made to the other device.

Figure 4:
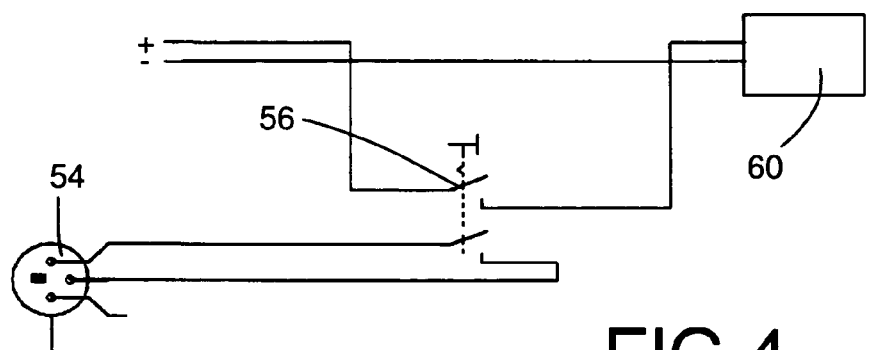
FIG. 4 is a view of an electrical connection to an external device that can be employed with the reminder device of FIGS. 1-3.

FIG. 4 shows and electrical schematic of another device with which this reminder device can be employed. FIG. 4 shows a double pole, single throw switch 56. One pole of this switch 56 is located between a power source and a device, such as an electric motor 60, that is powered by this power source. The other pole of the switch 56 is connected to an external device connector 54. When the double pole, single throw switch 56 is closed, the motor 60 is energized and a signal line to the connector 54 is closed. The line between the power supply and the motor 60 can be a high voltage line and the line to the connector 54 can be a low voltage line. Since the poles in the switch 56 are separate, the high voltage line and the low voltage lines remain separate and the only relationship is that they are both open or closed at the same time. An external device cable 22 extending between connector 56 on the external device and connector 20 on the reminder device will connect the low voltage side of switch 56 to the microprocessor. The microprocessor can be programmed to periodically poll this line to connector 20 so that when the switch 56 is closed or opened, this change of state will be detected by the reminder device. In this manner the time at which the switch 56 changes state is detectable by the reminder device 2, and these activation and deactivation times can be stored in memory 32 as part of a compliance file. The double pole, single throw switch 56 separates the signal line from the power source, so that the source of power to an external apparatus, such as a nebulizer compressor, is irrelevant to the use of the reminder device. Some nebulizer compressors are battery powered, while others are connected to line voltage. The configuration shown herein allows the same reminder device 2 to be used with either type nebulizer compressor, without any intervention by any user or supplier of the system or system components.

Assuming that the external device is a nebulizer and the motor 60 is a nebulizer compressor motor, the time when the user turns the nebulizer compressor on can be detected and stored and the time when that compressor is turned off can also be detected and stored. With these two times stored in memory, the interval during which the nebulizer was used can be determined along with the time when the use of the nebulizer began. Since the data stored in memory 32 is externally accessible, a medical professional can determine if a patient or care giver is properly administering the treatment. Use of this reminder device 2 thus allows a medical professional to monitor use of the nebulizer either contemporaneously with the treatments or historically. As will be explained the reminder device is accessible through a standard communications network, so a medical professional can access the memory when desired. However, the reminder device 2 is also portable so that it can be transported by the user of or care giver to the medical professional's premises. For instance the user can take the reminder device 2 to a doctor's office during a regularly scheduled visit, and the doctor will have a history of data representative of actual administration of the procedure available as a diagnostic tool. The user or care giver can also mail the reminder device to the medical professional or a periodic basis, and a replacement reminder device 2 can be supplied, so that the medical professional can evaluate the patient's actual care without the need of a connection to a communications network or a visit by the patient to the medical facility.

Figure 5:
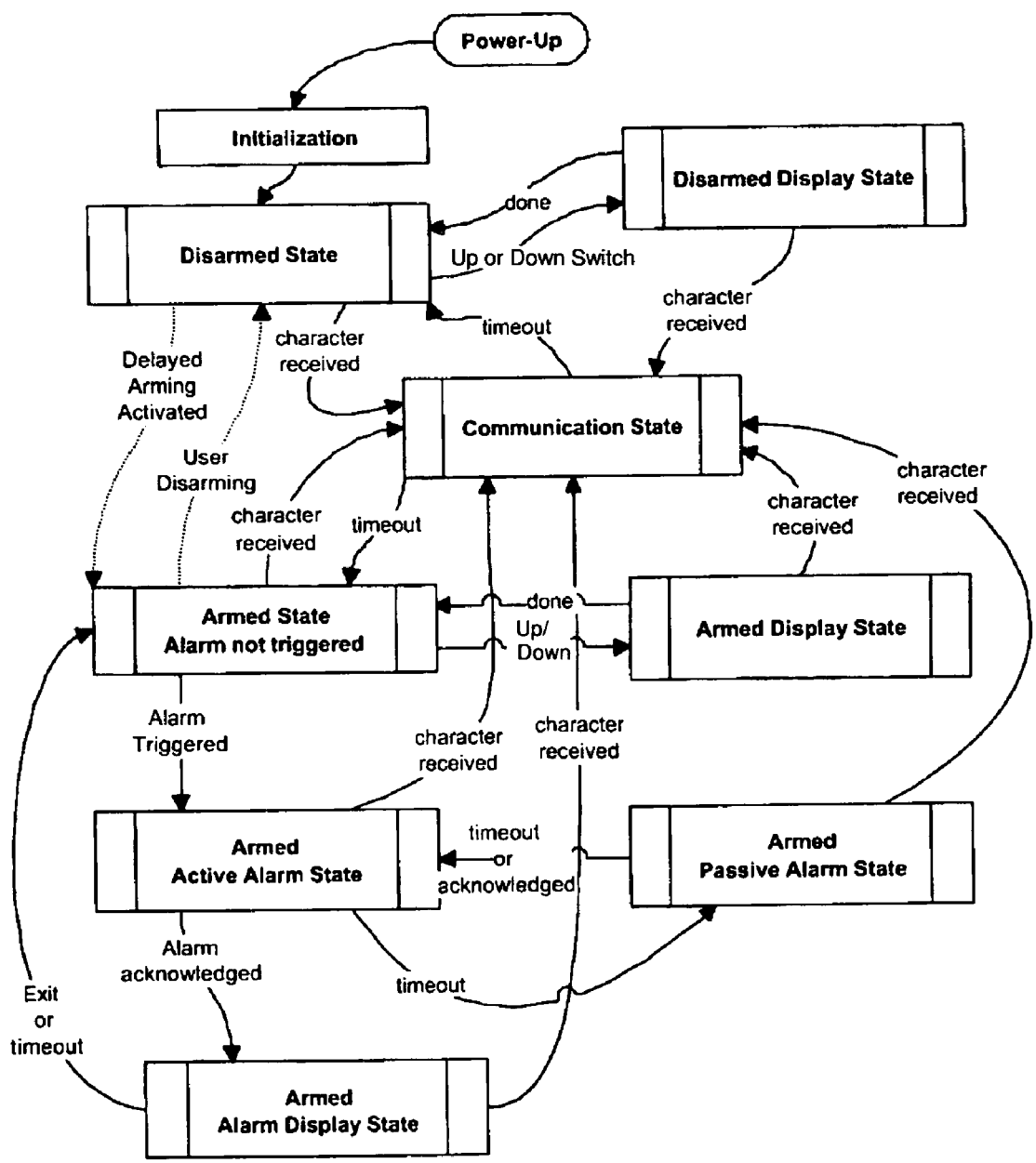
FIG. 5 is a view of a state diagram showing the primary operational states of the reminder device according to this invention.

FIG. 5 is an overall state diagram of the reminder device 2 showing the principal states during operation of a device in accordance with the schematic shown in FIG. 3. These states are implemented by programmed memory stored in ROM in the microprocessor employed to implement the reminder device. After power-up and initialization, the reminder 2 enters a disarmed state in which the reminder will receive and respond to commands, but in which it will not issue alarms or record or display data relevant to the performance of specified medical functions. While in the disarmed state, a user can display a messages stored in memory to a user or caregiver by depressing the Up switch 12 or the Down switch 14. The Up switch 12 is used to enter the Display Drugs Directory from the Disarmed State and the Down switch 14 is used to enter the Display Physicians Directory State from the Disarmed State. In each case the first item in the directory is displayed. In these states, the Up switch 14 will then scroll forward, and the Down switch 14 will scroll backward. To toggle from one directory to the other, the Acknowledgment switch 10 is pressed. After displaying this message, the reminder device 2 returns to the disarmed state after a pre-programmed interval as shown.

From the disarmed state, the reminder device 2 can enter the armed state or it can enter the communication state in which data is transmitted to or from random access memory under the control of the programmed microprocessor. When the reminder receives a character or characters through its external communication link, while in the disarmed state, the device enters the communication state. The reminder can also enter the communication state when a character is received over the external communication link while in the disarmed display state. After a prescribed timeout period, the device will return to the disarmed state in the event that the character or characters were initially received while the device was in the disarmed state or the disarmed display state. When in use the reminder is normally in the Armed State with the Alarm Not Triggered. In the normal operation the change from Disarmed State to Armed State and vice versa can be achieved only during the Programming State by programming certain locations in the reminder RAM. If those locations are unaffected, then the unit returns from the communication state into the state which it was in before. The reminder device 2 remains in the Armed State, Alarm Not Triggered, until the alarm is triggered at a preset time, which can be at pre-set intervals or which can be randomly set by programming instructions downloaded through the Communication State. While in the Armed State, Alarm Not Triggered State, activation of the Up Switch 12 and Down Switch 14, in a manner similar to that discussed with respect to the Disarmed State, causes the device to enter the Armed Display State in which pre-programmed messages can be displayed on an LCD display 8. In the Armed State, Alarm Not Triggered or in the Armed Display State, characters can be received through the external communications link, and the device can enter the Communication State. As in the Disarmed State, the device will return to the Armed State, Alarm Not Triggered when communication ceases unless the Alarm triggered while in the communication state.

When the alarm is triggered, the reminder device 2 enters the Armed Active Alarm State. The reminder device 2 is triggered at each pre-set time, and an audible or other sensory output notifies a user or caregiver that an appropriate act is to be performed, typically some medical procedure. If the alarm is acknowledged by pressing the Acknowledgment switch 10, while in the Armed Active Alarm State, the reminder device 2 enters the Armed Alarm Display State during which a pre-programmed message, corresponding to the activity denoted by the alarm is displayed on the LCD 8. Typically this message with remind a patient of the particular medical procedure required at that time. The user can exit this state by pressing the Acknowledgment switch 10 causing a return to the Armed State, Alarm Not Triggered, which is the normal state while waiting for the next alarm or alert. If the user does not acknowledge the Alarm within a specified period, during which the alarm is frequently enunciated, the reminder device 2 will enter the Armed Passive Alarm State, during which the Alarm will be enunciated at less frequent intervals. When the Alarm is acknowledged in the Armed Passive Alarm State, the device returns to the Armed Active Alarm State, where alarm acknowledgement and display is repeated as just described. After a specified timeout period, the reminder device will also return to the Armed Active Alarm State. If a character or characters are received over the external communications link, then the device will enter the Communications State from either the Armed Active Alarm State, the Armed Passive Alarm State, or the Armed Alarm Display State.

Figure 6:
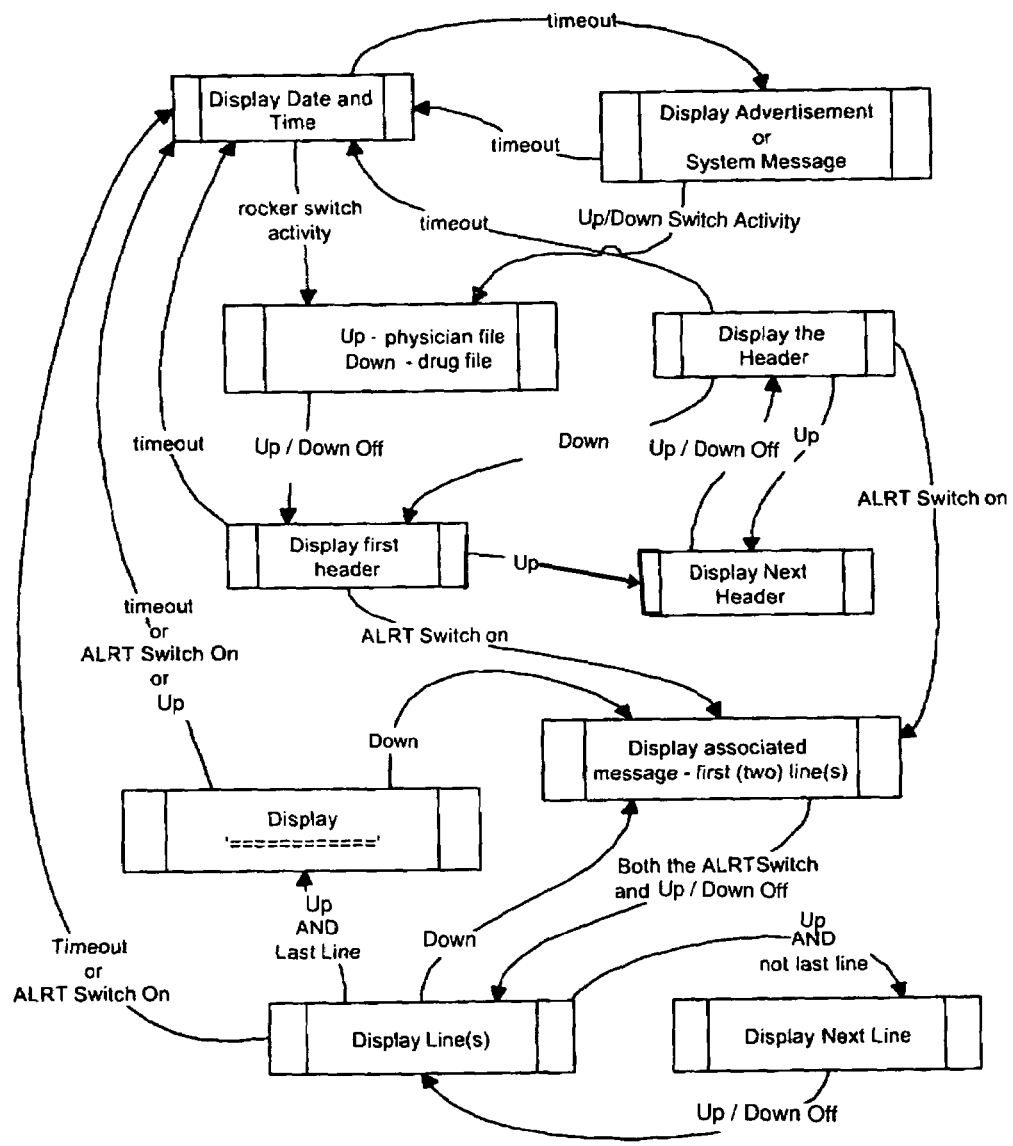
FIG. 6 is view of the Armed and Disarmed Display State Machine showing how this reminder device displays the appropriate message to the user.

The priority of events can be summarized as follows. At any time when the Alarm triggers, the state transfers into the Alarm State Machine. When communication is encountered, regardless of the state, then the current operation is suspended until communication ceases. Re-entry after communication or Alarm is always into the Display Date and Time State as will be described with reference to the Armed and Disarmed State Display Machines as shown in FIG. 6. Unless commanded by the program stored in memory, the normal display state message on the LCD 8 is the date and time. The display can be programmed to periodically display some other message, such as an advertisement or a system message, but the display will return to the standard date and time after an appropriately programmed timeout period. The Up and Down Switches can be used to alternatively display the physician file or the drug file preprogrammed in memory if they are activated while the device is in either of the two initial display states. After an appropriate period in which neither the Up switch 12 or Down switch 14 is activated the first header is displayed. Thereafter the Up switch 12 can be pressed to display the next header, which will appear after release of the Up switch 12. Subsequent activations of the Up switch 12 will cause the headers to sequentially display until timeout or until the Down switch 14 is activated, at which point the display 8 will return to the first header. Then after a prescribed timeout during which no activity occurs, the display will return to display date and time.

If the Acknowledgment switch 10 is activated during any of these display modes, that display state will switch to display the first two lines of a message associated with the displayed header. With the Acknowledgment switch 10, the Up Switch 12 and Down Switch 14 unactivated, the next line will then be displayed. To display subsequent lines, the Up switch 12 is activated, and if the displayed line is not the last line, subsequent activation of the Up switch will cause new lines to be displayed until the last line is displayed. To signify that the message is complete to blank lines will then be displayed in response to activation of the Up Switch 12. If the Down switch 14 is activated at any time during the display of this message, the display will return to the display of the first two lines of the message. In the event of the lapse of a timeout period during the progressive display of each message, the message display will be terminated and the display will return to the condition in which only the Date and Time are displayed. The display state also reverts to this original message if the Acknowledgment switch 10 is activated during the sequential display of the appropriate multilane message. Again, the Display State Machine functions are the same manner in either the Armed or Disarmed State.

Figure 7:
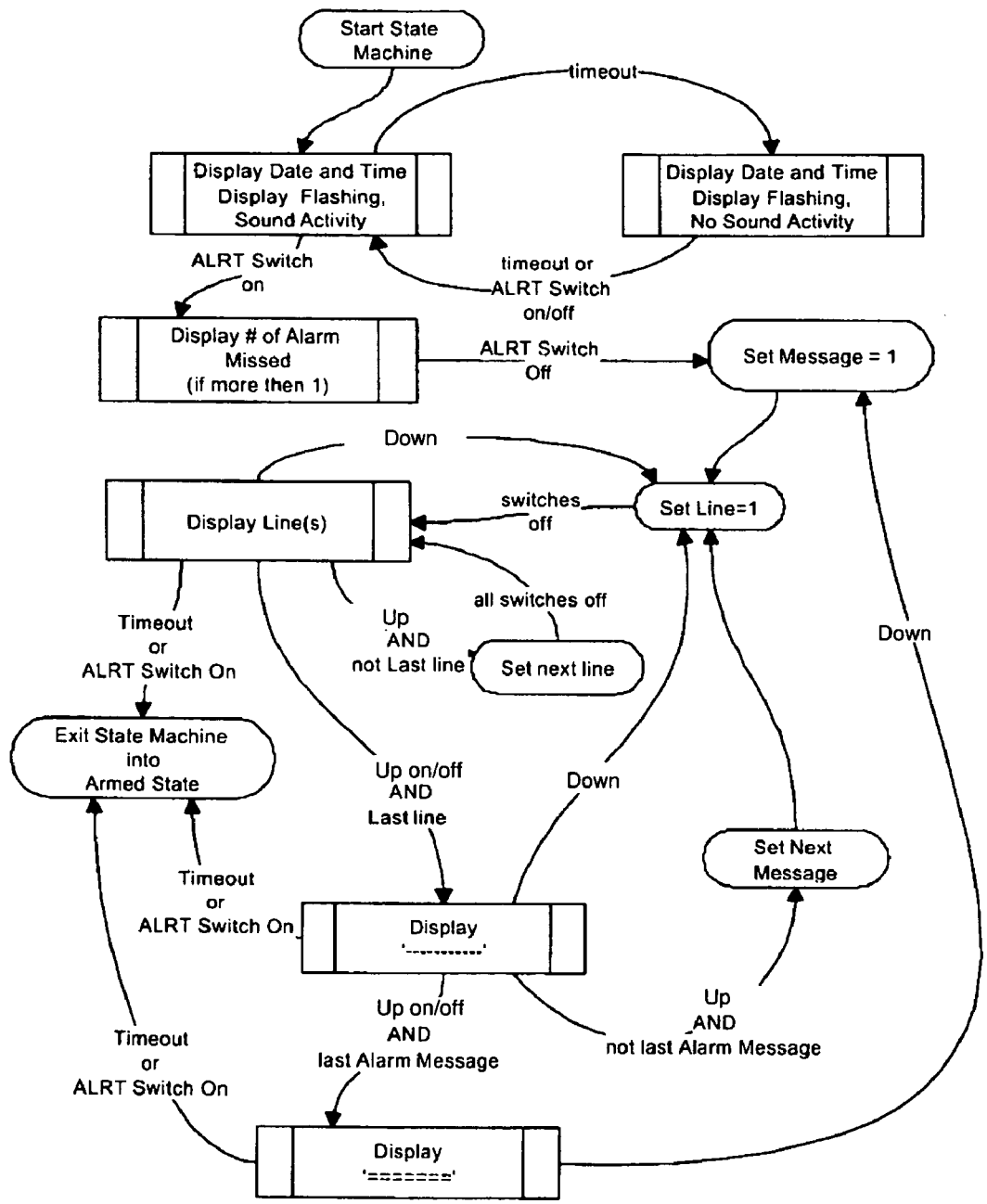
FIG. 7 is a view of the Alarm States State machine for this reminder device.

FIG. 7 shows more detail of the states when an alarm is activated at a pre-set time and date. The alarm starts this state machine. When the alarm is activated, a sound is emitted to notify the user of caregiver of a critical event, normally a scheduled time for a medical procedure. In the preferred embodiment a piezoelectric membrane element is used as a buzzer. Stored routines of the buzzer can produce different frequencies and durations. For instance a buzzer can emit a Hi Tone of approximately 2 kHz, a Mid Tone of approximately 1.6 kHz, and a Low Tone of approximately 1.35 KHz. In the preferred embodiment of the reminder device, the distinctive alarm sound is Mid Tone for 200 ms, Hi Tone for 200 ms followed by Mid Tone of 200 ms. A vibrator output may also be employed to alert a user of a scheduled event. In certain embodiments of this invention, for example when the reminder device is to be used not only to store the interval during which another device such as a nebulizer is used, the sound output is desired because the reminder device is connected to the other device and is not carried on the user's person. In addition to the sound alarm, the date and time display will begin flashing. Both the sound and the flashing display will continue for a specified period. In the preferred embodiment the active alarm consists of ten cycles, each of which comprises: LCD off, multi-tone alarm sound for 600 ms, followed by LCD on with a pause of 2370 ms before the next cycle begins. Of course this particular sequence is merely representative, and other sequences can be employed. For this example the total cycle time is three seconds so the Active Alarm State will continue for thirty seconds unless the alarm is acknowledged by pressing the Push-Button Switch during those thirty seconds.

If the Active Alarm is not acknowledged within thirty seconds, the state will change to the Passive Alarm State in which the date line is replaced by flashing "# Alarm(s)" message while the time display line is steady on, but the sound will be discontinued. In the first hour of the Passive Alarm State, the LCD will flash for a total of 190 cycles, with each cycle lasting for 2.5 seconds. During each such cycle the LCD line showing the number of triggered alarms will remain Off for 1.25 sec. and will be on for 1.25 sec. After the first hour in the Passive State, the Active Alarm State will happen less frequently for 290 cycles. Alarm information in the Reminder is stack-like structure of depth, which allows the reminder to store up to eight Alarms. If more than eight Alarms occur without acknowledgement and the ninth alarm triggers, then the first Alarm drops out from the Alarm stack and that Alarm will be stored as never acknowledged.

When an Alarm is acknowledged in the Active Alarm State, the first message is either the message of the last Alarm or any downloaded message that may be pending. The message is displayed when all switches 10, 12, 14 are off. Pressing the Up switch 12 causes the message scroll line to line until the last line is reached when a dashed "------" line is displayed. The Up Switch 12 can then be pushed and if the message is the last pending message, the display will show two dashed "=====" lines. After a time out or after the Acknowledgment switch 10 is pressed, the device will exit the Alarm State and return to the Armed State. If there are additional pending messages, pressing the Up switch 12 will cause the device to proceed to the next pending message. To repeat a message, the Down switch 14 can be used to return to the first line in the pending message. When communication is encountered then the Alarm State Machine is suspended.

The reminder device 2 according to this invention is configured using a computer interface so that the device may be configured either remotely over a communications network or by connecting the device directly to the computer on which the specific interface is active. In either event data is downloaded to the programmed reminder. A number of different types of data can be downloaded to the reminder device memory. Examples of the type of data that can be downloaded include the following:

Periodic Alarm times with associated patient friendly instructions;

Random Alarm Dates/Times is associated instructions;

Revolving Alarms times with intervals of from one minute to two months;

Patient compliance evaluation times;

One time messages for the patient;

Advertisements and System messages;

List of drugs and instructions related to their use;

List of physicians and their instructions;

Descriptors of records for attachable medical instruments.

Figure 8:
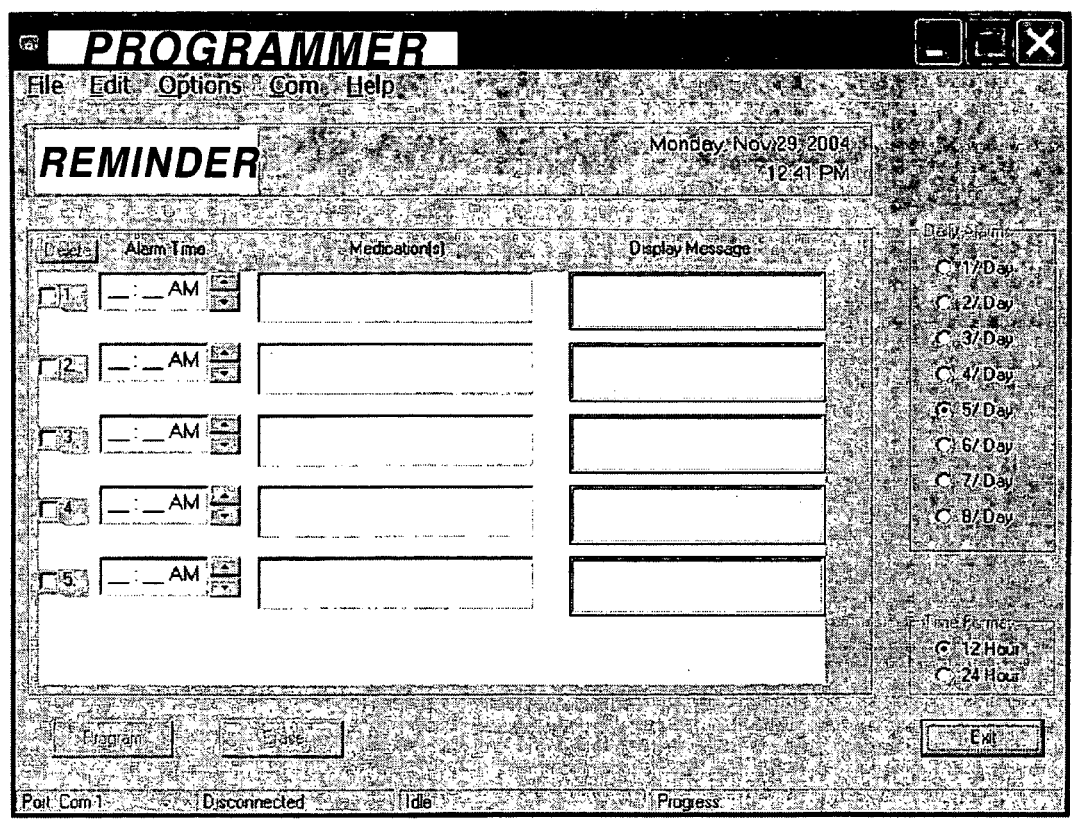
FIG. 8 is a view of a programming input page screen that can be employed to program the reminder device.

FIG. 8 shows one screen that would be displayed on the computer interface that is used to configure the reminder device 2. From this programmer screen, five different alarms times can be programmed into a reminder device in communication with a computer on which the configuration software, including this programming screen, is resident. Using this screen, up to eight different times can be programmed each day. The particular medication can be specified and a message to be displayed on the LCD corresponding to each alarm can be entered. In this way the reminder device can be configured by a computer literate person possessing sufficient medical skill to determine an appropriate schedule for administering medications or performing other medical treatments. The user is not required to perform complex configuration tasks. The user only has to respond to the messages and instructions, primarily by using the acknowledgment switch 10.

Data stored in the reminder memory 32 can also be uploaded to a medical professional. Typical examples of uploaded data could include the following:

Periodic Alarm Patient Compliance Files, showing how reliably the patent has responded to these alarms;

Random Alarm Patient Compliance Files, showing a similar response history;

Attachable medical instrument date/time/values records, specifically showing the intervals in which an attached nebulizer or similar apparatus was used.

Pill box activity file for those configurations in which the switch 21 is used instead of a connection to an external device.

The reminder device need not be capable of analyzing the data stored in memory. When data is uploaded to a computer containing appropriate analysis software, that device can be used to present the information in a manner suitable for use by a medical professional. All the user or patient or his or her care giver must do is to either transport the reminder device 2 to the medical professional or attach the reminder device to a communications interface, such as modem 40 for uploading the stored data. The modem can be supplied with means by which the user can establish a connection with a central database. For example, the modem can include a single switch, which will initiate the connection when pressed by the user. Alternatively, the communication can be initiated by the system administrator through the modem 40 to the reminder device 2. All that would be required of the user is to connect the reminder device 2 to the modem. If the user is employing the device in a portable mode, a message and associated alarm can be stored in memory to remind the user to connect the reminder device at an appropriate time. Communication can be established over a telephone line that is used for other purposes, in a manner that would be clear to one of ordinary skill in the art. The communication network could be either through a standard telephone network or it could employ a TCP/IP protocol so that communications could be carried out through the Internet.

Figure 9:
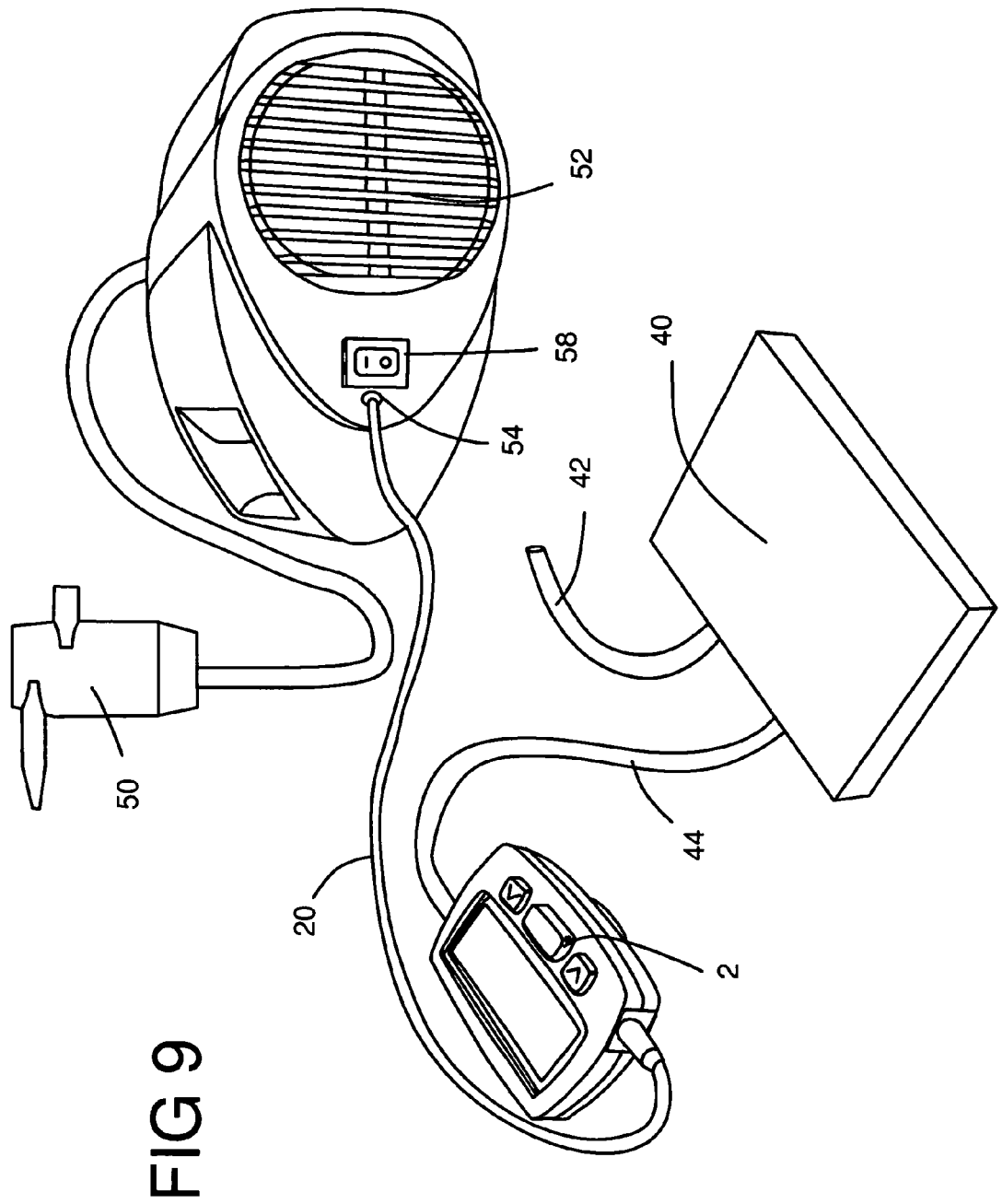
FIG. 9 is a view showing how this reminder device can be used with an external medical device, such as a nebulizer and nebulizer compressor, for communications over a telecommunications network.
Figure 10:
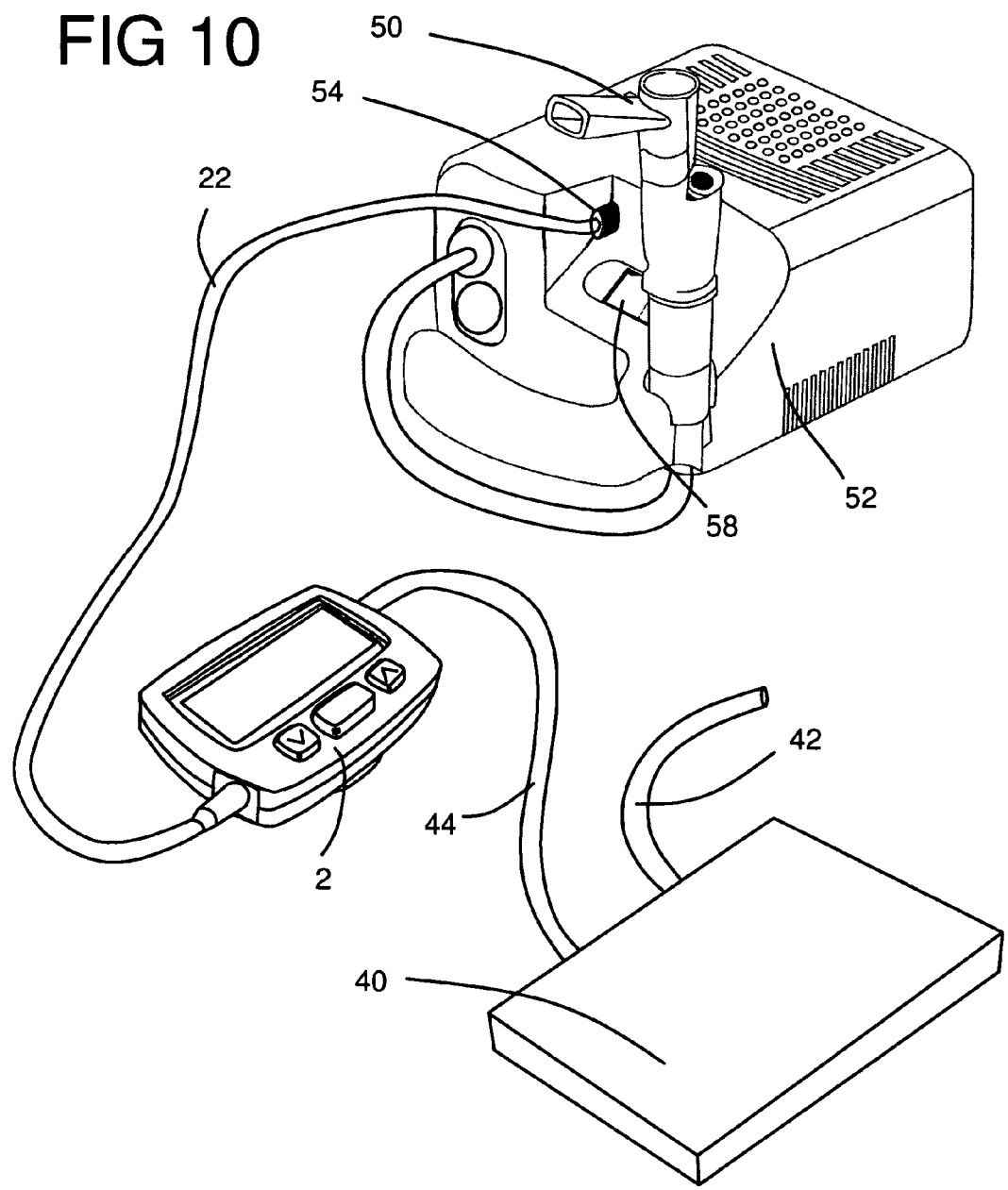
FIG. 10 is a view showing how this reminder device can be used with another nebulizer and nebulizer compressor device.

FIGS. 9 and 10 show the manner in which the reminder device can be connected between the reminder device 2 and both a modem 40 and a nebulizer compressor 52. The modem is connected to a communications network through a communications link 42 and to the reminder device 2 by a cable 44. The reminder device is in turn connected to the nebulizer compressor by a cable 20 having standard connectors on each end for connecting to the device connectors 20 and 54. The only changes to a standard nebulizer compressor would be incorporation of a connector 54 and a signal lines connecting a new double pole single throw switch 56 to this connector 54. The compressor switch actuator 58 can be identical to a standard with actuator used on a standard nebulizer compressor. Each of the nebulizers shown in FIGS. 9 and 10 are otherwise standard compressor units and can be used apart from the reminder device 2 in the same manner as a user would employ the nebulizer 50 to dispense vapors for treating the patient in the same manner as before. The inexpensive modifications to the nebulizers thus do not make its use without the reminder device capabilities prohibitive or too costly. The reminder device 2 and this monitoring system thus supplies an additional capability to existing nebulizer devices. In the preferred embodiment only the on/off status of the nebulizer compressor switch 56 is monitored. It is understood, however, that additional operational characteristics could be monitored, but more substantial modifications would need to be made to the nebulizer compressors.

FIG. 11 shows an alternate embodiment of a reminder device 102, similar to reminder device 2. Reminder device 102 includes and LCD screen 108 and three switches 110, 112 and 114 that correspond to switches 10, 12 and 14 of the first embodiment. This reminder device 102 includes a single connector 120 in the form or a subminiature D connector. The reminder device 102 can now be connected directly to a nebulizer or other device employing a similar connection. Alternatively, the reminder device can be connected to a communications unit 140 shown in FIG. 12, which is composed of two parts, a communication unit and a modem for transmission or reminder data to the central data base over line 142. In addition the reminder device 102 can be connected directly to a personal computer through a serial port or to a medical diagnostic device. If the reminder device is plugged into the communications unit 140 through connector 144, it can in turn be connected to a nebulizer or other medical treatment unit through connector 145. Alternatively the reminder device can be connected to other medical diagnostic devices. When the reminder device 102 is connected to the communications unit 140, the communications unit 102 can then be connected to a data base through the modem connection 142 via an automatic dial-up feature to transfer data to the data base. It should be understood, however, that the reminder device 102 can be connected through communications unit 140 directly to medical treatment devices, such as nebulizers, or to medical diagnostic devices without being connected through the modem, which forms only part of the communications unit 140.

Another alternative version of this invention would be to incorporate the reminder device and the nebulizer compressor into one physical device. This approach would require greater modifications to a conventional nebulizer compressor, but the majority of the nebulizer related functions could still be accomplished. The reminder functions could, however, be incorporated into the nebulizer compressor without any direct encroachment on the operation of the nebulizer compressor or the nebulizer itself. Of course, the portability of the reminder device would be compromised by this approach. A reminder device incorporated into the nebulizer compressor could still be conceptually employed by the patient or caregiver to monitor other medical procedures or medication schedules, but the ease of use for procedures not involving the use of a nebulizer would probably be compromised.

The switch status monitored by the reminder device does not have to be the nebulizer compressor ON/OFF switch as contemplated by the preferred embodiment of the invention. Other operational characteristics of the nebulizer or nebulizer compressor could be monitored. For example, air flow or electric current in the nebulizer compressor could also be monitored. It would also be possible to determine if the nebulizer compressor was operational by directly sensing the electrical current powering the motor. If current is sensed, a switch could be automatically closed, and the reminder device could sense the status of that switch. If air is flowing from the compressor to the nebulizer, a flow sensor can activate a switch, and the reminder device could sense the status of that switch. In neither of these two alternative approaches would the user need to directly activate the switch dependent on current or airflow. All the user would do would be to turn on the nebulizer compressor in a conventional manner, and normal operational characteristics of the device would then be monitored.

The medical reminder system, including the medical reminder device can also be used with medical treatment devices other than a nebulizer. For example, the reminder device can be used with devices for applying heat radiation therapy radiation, which could be monitored by the reminder device in substantially the same way that it would be used to monitor use of a nebulizer. The reminder device can also be used with medical diagnostic devices, such as a digital high blood pressure monitor. A reminder device can be used to store readings input from digital medical instruments having digital outputs, such as a digital scale, digital blood pressure monitors, digital pulse monitors, digital instruments for measuring glucose levels in the blood of a diabetic patient, digital thermometers or digital instruments for measuring oxygen levels in the blood, among other examples. In the preferred embodiment, the reminder device is especially suited for relatively simple medical diagnostic instruments, and the preferred embodiment is suited for storing up to eight values per treatment session. Other procedures, which generate significantly greater amounts of data are not suited for use with the preferred embodiment of this invention, although other larger embodiments of the same invention could support data collection from such procedures if appropriate.

The various embodiments of this invention depicted herein are intended to be representative, and it would not be possible to include all possible modifications that would be apparent to one of ordinary skill in the art. Therefore the scope of this invention is defined by the following claims and is not limited to the representative embodiments depicted herein.

The invention claimed is:

1. A programmable reminder device for use in reminding a user of a scheduled medical procedure and for storing data characteristic of actual performance of the scheduled medical procedure, the device comprising:
    a microprocessor
    read only memory including instructions for operation of the reminder device:
    read/write memory for storing times for performance of scheduled medical procedure, information identifying the medical procedure, and data characteristic of actual performance of the medical procedure;
    a visible display in communication with the microprocessor, for displaying information identifying the medical procedure;
    an alarm for prompting a user to begin the scheduled medical procedure;
    a switch for acknowledging the alarm; and
    an input connection on the reminder device connectable to a medical apparatus used in performing the medical procedure, data characteristic of actual performance of the scheduled medical procedure and operation of the medical apparatus being input through the input port and being storable in the read/write memory, wherein the input connection is connected to the apparatus performing the medical procedure and the data characteristic of actual administration is generated by the apparatus and input to the reminder device.

2. The programmable reminder device of claim 1 including a second input connection through which times for performance of scheduled medical procedure and information identifying the medical procedure can be downloaded to the read/write memory.

3. The programmable reminder device of claim 2 in which multiple times for administration of different medical procedures and information identifying different medical procedures are downloadable and storable in the read/write memory.

4. The programmable reminder device of claim 3 in which data representative characteristic of actual administration of only one type of scheduled medical procedure is storable in read/write memory.

5. The programmable reminder device of claim 1 wherein data characteristic of periodic actual administration of a medical procedure is storable in the read/write memory to construct a history of actual administration of the medical procedure.

6. The programmable reminder device of claim 1 wherein the visible display comprises a liquid crystal display.

7. The programmable reminder device of claim 6 including switches for scrolling lines on the liquid crystal display.

8. The programmable reminder device of claim 1 wherein data characteristic of actual administration of the medical procedure comprises a time interval between actuation of a separate apparatus for performance of the medical procedure and deactivation of the separate apparatus.

9. The programmable reminder device of claim 8 including a cable connectable to the input port and to switch means on the separate apparatus wherein the time interval between actuation and deactivation of the separate apparatus comprises the time interval between actuation and deactivation of the switch means.

10. The programmable reminder device of claim 1 wherein data characteristic of actual performance of the medical procedure is stored in the read/write memory for a plurality of successive performances of the same medical procedure.

11. A system for use in collecting data representative of administration of medical procedures and characteristic of actual performance of at least some medical procedures by a user and for transmitting such data to a medical professional for subsequent review of the course of administration of the medical procedures, comprising:

a programmable reminder device including a microprocessor, read only memory including instructions for operation of the reminder device, and read/write memory for storing times for administration of scheduled medical procedures and actual performance of at least some medical procedures, information identifying the medical procedures, and data representative of administration of the medical procedures;

an alarm on the programmable reminder device for notifying a user of scheduled times for administration of medical procedures stored in the read/write memory;

an acknowledgment input on the programmable reminder device actuatable by a user to denote receipt of the alarm, the time of each acknowledgment input being stored in the read/write memory; and a communications interface device connectable to the programmable reminder device and to an external communications network for downloading times for administration of scheduled medical procedures and information identifying the medical procedures to the programmable reminder device, and for uploading data stored in the read/write memory representative of alarm times and acknowledgment times for corresponding medical procedures and characteristic of actual performance of at least some medical procedures in response to a downloaded request submitted through the external communications network.

12. The system of claim 11 wherein the alarm is initially activated at the time for administration of each scheduled medical procedure and subsequently in the absence of an acknowledgment input, the time between the first alarm for a specific scheduled medical procedure and the first acknowledgement being stored in read/write memory regardless of subsequent alarms.

13. The system of claim 12 wherein the times for alarm activation and acknowledgment for a specific scheduled medical procedure are stored in read/write memory as corresponding data regardless of intervening alarms for other medical procedures stored in reminder device.

14. The system of claim 11 wherein the reminder device is connectable to an external medical apparatus used to perform a medical procedure, the actual times of operation of the external apparatus being storable in read/write memory in conjunction with an alarm time for the same medical procedure.

15. The system of claim 11 wherein the reminder device is battery powered, portable, and disconnectable from the communications interface device, so that the reminder device can be transported to a medical professional to upload data representative of administration of medical procedures.

16. A system for storing data representative of administration of a scheduled medical procedure in which an electrically powered medical apparatus is used to perform the medical procedure, the system comprising:

an on/off switch on the electrically powered medical apparatus;

a separate electronic device connectable to the electrically powered medical apparatus by cable means, and including accessible memory, and an alarm for notifying a user according to the schedule for administering the medical procedure;

the cable means being connected to the electrically powered medical apparatus so that a signal is transmitted to the electronic device when the on/off switch on the electrically powered medical apparatus is activated to perform the medical procedure, the times of actuation of the on/off switch being stored in the accessible memory so that that interval during which the scheduled medical procedure is performed can be retrieved from memory; and an acknowledgment switch on the separate electronic device which is actuated at the time the scheduled medical procedure is initiated so that the stored interval can be associated with the correct medical procedure.

17. The system of claim 16 wherein the electrically powered medical apparatus comprises a nebulizer and associated nebulizer compressor, the on/off switch being on the nebulizer compressor.

18. The system of claim 17 wherein the on/off switch comprises a double pole, single throw switch so that the same switch can switch line voltage to the nebulizer compressor and a signal voltage on the cable extending between the nebulizer compressor and the separate electronic device.

19. The system of claim 17 wherein the separate electronic device can be connected to an external communications network so that stored intervals can be transmitted to a remote medical professional for analysis of use of the nebulizer.

20. The system of claim 17 wherein the separate electronic device is portable and disconnectable from the nebulizer compressor so that the separate electronic device can be transported to a medical professional for analysis of use of the nebulizer.

21. A programmable reminder device for use in reminding a user of a scheduled medical procedure and for storing data characteristic of actual performance of the scheduled medical procedure, the device comprising:
- a microprocessor
- programmable read only memory including instructions for operation of the reminder device:
- read/write memory for storing times for performance of scheduled medical procedure, information identifying the medical procedure, and data representative of actual performance of the medical procedure;
- a visible display in communication with the microprocessor for displaying information identifying the medical procedure;
- an alarm for prompting a user to begin the scheduled medical procedure;
- a switchable user actuated input for acknowledging the alarm; and
- the reminder device being connected to a switch on an apparatus used in performing the medical procedure, the status of the switch, indicative of actual performance of the scheduled medical procedure otherwise independent of the reminder device, being detected by the reminder device and being storable in the read/write memory.

22. An apparatus for dispensing vapors to treat a patient comprising:
- a nebulizer;
- a nebulizer compressor to which the nebulizer is attachable;
- an output on the nebulizer compressor, the output having a state indicative of actual operation of the nebulizer compressor:
- a device receiving the output of the nebulizer compressor and storing times when the nebulizer compressor is in operation so that a record of times in which the nebulizer is in use in maintained by monitoring use of the nebulizer compressor.

23. The apparatus of claim 22 wherein the state indicative of actual operation of the nebulizer compressor is the state of an on/off switch on the nebulizer compressor.

24. The apparatus of claim 23 wherein the on/off switch on the nebulizer compressor comprises a double pole, single throw switch, a first pole being between a power source and the nebulizer compressor, the second pole being connected to the output.

* * * * *